United States Patent [19]
Törnblom

[11] 3,971,982
[45] July 27, 1976

[54] PLURAL FREQUENCY MULTI-PHASE TRANSDUCER ARRANGEMENT FOR DETECTING THE PRESENCE AND LOCATION OF FAULTS IN A METAL BODY AND COMPENSATING FOR BODY MOVEMENTS

[75] Inventor: Bengt Törnblom, Vasteras, Sweden

[73] Assignee: Allmanna Svenska Elektriska Aktiebolaget, Vasteras, Sweden

[22] Filed: Apr. 30, 1975

[21] Appl. No.: 573,252

Related U.S. Application Data

[63] Continuation-in-part of Ser. No. 570,619, April 23, 1975, abandoned, which is a continuation-in-part of Ser. No. 480,427, June 18, 1974.

[30] Foreign Application Priority Data
Apr. 23, 1974 Sweden.............................. 7405409

[52] U.S. Cl. ............................................... 324/37
[51] Int. Cl.² ........................................ G01R 33/12

[58] Field of Search................................. 324/37, 40

[56] References Cited
UNITED STATES PATENTS
2,065,118  12/1936   Davis, Jr............................... 324/40

*Primary Examiner*—Robert J. Corcoran
*Attorney, Agent, or Firm*—Kenyon & Kenyon Reilly Carr & Chapin

[57] ABSTRACT

Improved apparatus for detecting and locating defects in metal bodies of the type in which the body under test is difficult to keep centered in which a multiphase transducer coil induces currents in the body which are detected by a secondary transducer coil providing fault and position information. In the preferred embodiment two different frequencies are induced with one frequency used to compensate the other for variations with respect to a central location within the confines of the secondary coil.

1 Claim, 3 Drawing Figures

PLURAL FREQUENCY MULTI-PHASE TRANSDUCER ARRANGEMENT FOR DETECTING THE PRESENCE AND LOCATION OF FAULTS IN A METAL BODY AND COMPENSATING FOR BODY MOVEMENTS

RELATED APPLICATIONS

This application is a continuation-in-part of Ser. No. 570,619, filed Apr. 23, 1975 now abandoned which is a continuation-in-part of application Ser. No. 480,427 filed Jun. 18, 1974.

BACKGROUND OF THE INVENTION

This invention relates to the testing of metal bodies for defects in general and more particularly to an improved testing device for detecting defects in a metal body where the body is moved during testing and cannot be reliably maintained in an accurate position with respect to the testing device.

Co-pending Application Ser. No. 480,424 describes apparatus for detecting defects in a metal body by generating a traveling field such as a rotating or a linearly traveling field in the body being tested and by providing means to sense an asymmetry in the resulting magnetic field occurring due to the induced eddy currents thereby permitting determination of the location and nature of the fault from the electrical signals. In the embodiment disclosed therein faults and irregularities in the body such as cracks, indentations and so on are detected through this asymmetry which is preferably indicated in a neutral line existing between the generator and the transducer. In another embodiment a bridge or differential connection is used.

However, the device claimed therein is not usable for all types of testing which must be carried out. It has been found that for certain types test objects, for example, rolled wire other movable test objects, it is very difficult to keep the test object centered with respect to a differential connection or the like as is necessary with the majority of embodiments disclosed and claimed in the aforementioned application. In view of this, the need for an improved device which can make accurate measurements in such test objects becomes evident.

SUMMARY OF THE INVENTION

The present invention solves this problem. To accomplish this, a multi-phase transducer arrangement disclosed but not claimed in the aforementioned patent application is arranged to surround the object under test. Associated with the transducer, which induces eddy currents in the object, is a secondary transducer in form of at least one coil surrounding the object. The secondary transducer coil will provide an output which can indicate both the position of the object under test with respect to the axis of the coils and can develop error signals indicating faults in the object. In the preferred embodiment two frequencies are used to induce currents into the test object. The two frequencies detected by the secondary transducer are then filtered and the one frequency used to develop correction signals to correct for errors in the second signal due to position displacement from the axis, in the second signal. As a result the signal at the second frequency will accurately reflect only the faults in the test object.

DETAILED DESCRIPTION OF THE PREFERRED EMBODIMENT

Figure 1:
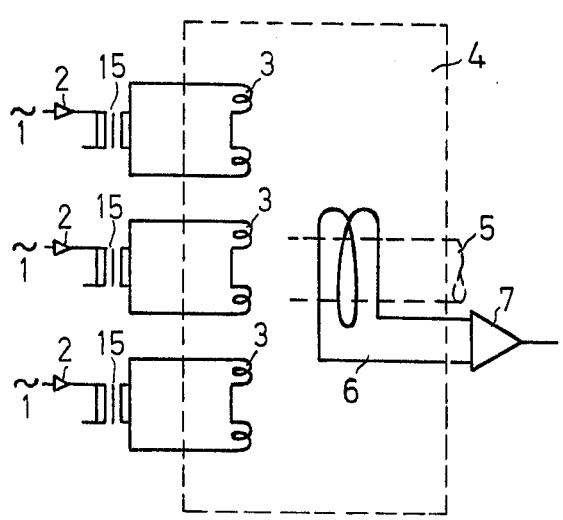
FIG. 1 is an electrical schematic of a primary and secondary transducer coil arrangement according to the present invention.
Figure 2:
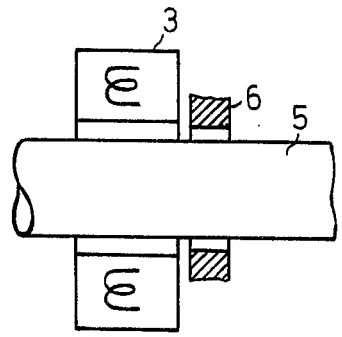
FIG. 2 is a mechanical schematic of the coil arrangement of FIG. 1.

As illustrated by FIG. 1, an appropriate generator provides a three-phase current indicated schematically by 1 to three identical amplifiers 2, each of which is coupled to the primary of a transformer 15. The secondary of each of the transformers 15 is coupled to a transducer coil 3. The transducer coils 3 will be spaced around the test object 5 symmetrically much in the manner shown in connection with FIG. 2a of the aforementioned application, i.e. they will be spaced at 120° increments. This arrangment is illustrated schematically in FIG. 2. Adjacent to the primary transducer circuit made up of the coils 3 is a secondary transducer coil 6 which surrounds a test object 5. Its location relative to the coils 3 is illustrated on FIG. 2. Coil 6 comprises a single differential coil provides an output to an amplifier 7, preferably a differential amplifier to provide a final output signal. As noted above, the test object 5 may be a rolled wire or rod wire and must be tested while moving through the coils. Such a wire or rod cannot be reliably maintained centered on the axis of the coils. The disclosed arrangment will cause an output signal from amplifier 7 in which the output voltage is proportional to the radial position of the test object relative to the coil and the phase angle is proportional to the angular position, i.e. the voltage represents how close any portion of said object 5 is to the transducer coils 3 and 6 and the phase represents at which point about the inner circumference thereof the rod is closest. This information will, of course, be supplied independently of whether or not faults are present. Furthermore, it is independent of the particular test frequency chosen. That is, simply for obtaining information with regard to position the choice of frequency is relatively uncritical. Because of the nature of these signals it then becomes possible to make determinations as to faults should the signal deviate from predetermined limits. It should be noted, that the coil 6 may be, instead of a single coil, a plurality of coils. Furthermore it need not be positioned adjacent the primary transducer coils 3 but may also be located inside those coils.

Figure 3:
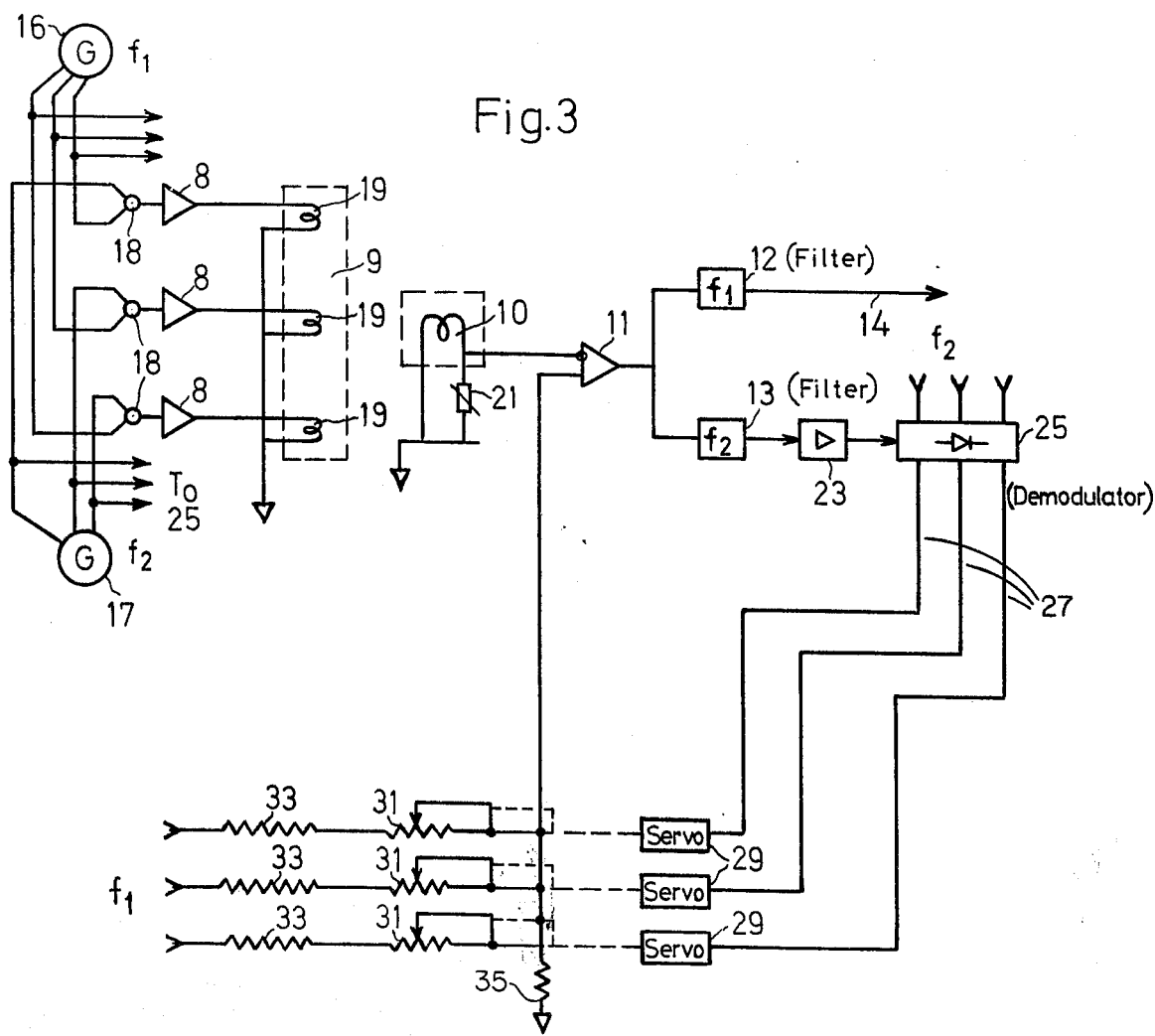
FIG. 3 is a schematic illustration of a further embodiment of the present invention which permits developing accurate output information through the use of two frequencies.

FIG. 3 shows a particularly advantageous embodiment of the present invention. In this embodiment generators 16 and 17 having respective frequencies f1 and f2 are provided. Each of the generators is a three-phase generator and an output from each of the generators is provided to each of three amplifiers 8. The two frequencies are summed at a summing junction 18 at the inputs of the respective amplifiers 8. The amplifier outputs are provided to respective transducer coils 19 having their other side grounded. Once again the transducer coils 19 will be arranged about the test object in the manner described above in connection with FIGS. 1 and 2. The currents induced by these coils in the object are detected by secondary transducer coil 10. Associated therewith is a variable resistor 21 used for initial calibration purposes. The voltage developed therein is taken off across the resistor and provided to an amplifier 11. Amplifier 11 has a second correction input to be described in more detail below. The output of amplifier 11 is provided to respective filters 12 and 13. Filter 12 is designed to pass only the frequency f1 and filter 13 only the frequency f2. The output of filter 13, is then provided to an amplifier 23 for further amplification of the signal. The output of amplifier 23 is provided to a phase sensitive demodulator 25 having as synchronizing inputs the three phase outputs of the generator 17. In the phase sensitive demodulator 25 the three components of the detected signal at frequency f2 will be demodulated to provide respective d-c outputs on the lines 27. It will be recognized that these d-c outputs will accurately represent the position of the test object within the coils. These outputs are used as inputs to conventional servo systems 29 which have outputs driving wipers on a plurality of potentiometers 31. The potentiometers 31 are in series with fixed resistors 33 having respective inputs from the generator 16 at the frequency f1. These inputs are all summed on a line 35 and provided as second input to the amplifier 11. Initially, the inputs through the variable resistor 31 can be set so that the inputs at frequency f1 are just equal to but of opposite polarity to the inputs from the coil 10. This will result, where no defects are present and the test object is centered, in a zero ouput on the line 14 from filter 12. That is to say, if there are no faults present and the test object is symmetrically positioned, the outputs on lines 27 from phase sensitive demodulator 25 will all be equal. As a result, the potentiometer settings 31 will all be equal and the same zero correction input will be provided for all three-phases of f1 to cancel out those three phases. If the test object deviates so as to come closer to one of coils, the f2 output for that coil, i.e. that phase, will increase correspondingly and the d-c output from the demodulator 25 will result in an increase in the amount of the f1 correction signal provided for that phase. This will then offset the increased experience at the input of amplifier 11 because of the test object being closer to the coil associated with that phase and, in the absence of errors, there will still be no output on the line 14. Thus, in all cases the position of the rod or wire within the coil is corrected at the frequency f1. If a fault does occur, the output at frequency f1 will deviate from zero and can be readily detected. This is true even though the frequency f2 also responds. Although only two frequencies are shown here with the frequency f2 being used for zero balancing, the reverse could be done, i.e. the frequency f1 could be used to balance the frequency f2. In addition, if more than two frequencies are used, similar balancing can be carried out. In selecting the frequencies to be used, the fact that faults appear differently at different frequencies can be used. This fact along with the fact that position information is relatively indendent of frequency permits operation of the arrangement. Thus, the frequency used to develop correction signals can be one which does not respond particularly well to faults whereas the frequency f1 for use in actual fault detection will be selected as one at which a particularly pronounced effect occurs should a fault be present. As a result, because the frequency f2 responds to the fault differently than the frequency f1 the compensation provided because of a fault will not be of the proper magnitude to properly offset the frequency f1. As a result, the fault will be accurately detected. Thus, in essence the present invention makes use of the fact that, with regard to position, frequency does not particularly matter but that different frequencies do respond differently to defects. In other words, if compensation signals are developed at one frequency they can be used accurately to compensate a second frequency for position errors. However, in responding to fault there is a significant difference in the response at the two frequencies so that even if the frequency being used to develop correction signals responds it will not respond in the same way as the frequency providing the fault detection output and an accurate indication will be given. It should be further noted that the secondary coil 10 or secondary coil 6 should be thought of as a differential connection since with the test object centered the sum of its induced EMFs will be zero.

Thus, an improved fault detection apparatus has been shown and described. Although a specific embodiment has been shown it will obvious to skilled in the art that various modifications may be made without departing from the spirit of the invention which intended solely by the appended claims.

I claim:
1. Apparatus for testing metal bodies comprising:
   a. a first multi-phase generator having a first frequency:
   b. a second multi-phase generator having the same number of phases as said first generator but having a different frequency;
   c. means for summing the outputs of said first and second multi-phase generators;
   d. a first plurality of transducers coils comprising at least one coil for each phase of said first and second multi-phase generators, the individual coils being coupled to the individual phase outputs of said means for summing so as to induce a moving field in said body when fed with a multi-phase current from said multi-phase generator;
   e. a single secondary coil surrounding said metal body, said secondary coil detecting variations in the magnetic field generated by said transducers coils which occur when faults and irregularities in the body being tested are encountered; and means responsive to the output of said secondary coil at one of said frequencies for correcting the output of said secondary coil at the other frequency for variations of the position of the test object within said secondary transducer coil.

* * * * *

UNITED STATES PATENT AND TRADEMARK OFFICE
CERTIFICATE OF CORRECTION

PATENT NO. : 3,971,982
DATED : July 27, 1976
INVENTOR(S) : Bengt Törnblom

It is certified that error appears in the above-identified patent and that said Letters Patent are hereby corrected as shown below:

Column 1, line 40 after "rolled wire" insert -- and --.

Column 2, lines 28 and 29 change "comprises" to read "comprising".

Signed and Sealed this

Sixteenth Day of November 1976

[SEAL]

Attest:

RUTH C. MASON
*Attesting Officer*

C. MARSHALL DANN
*Commissioner of Patents and Trademarks*